(12) United States Patent
Kinoshita et al.

(10) Patent No.: US 7,329,246 B2
(45) Date of Patent: Feb. 12, 2008

(54) DISPOSABLE WEARING ARTICLE HAVING MULTILAYERED CORE COMPRISING CONVEX GAPS AND V-SHAPED CUTOUTS

(75) Inventors: Akiyoshi Kinoshita, Kagawa (JP); Yoshio Ono, Kagawa (JP); Tomoko Tsuji, Kagawa (JP); Akiko Yagi, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 0 days.

(21) Appl. No.: 10/850,445

(22) Filed: May 21, 2004

(65) Prior Publication Data

US 2005/0148988 A1    Jul. 7, 2005

(30) Foreign Application Priority Data

May 22, 2003   (JP) .............................. 2003-144764

(51) Int. Cl.
    *A61F 13/15*   (2006.01)
(52) U.S. Cl. ............... 604/396; 604/383; 604/385.101; 604/385.23; 604/385.12
(58) Field of Classification Search ............... 604/383, 604/396, 385.101, 385.23, 385.12, 378–380, 604/385.01; D24/124, 126
    See application file for complete search history.

(56) References Cited

U.S. PATENT DOCUMENTS

| | | | | |
|---|---|---|---|---|
| 3,860,003 | A | * | 1/1975 | Buell ..................... 604/385.25 |
| 4,790,839 | A | * | 12/1988 | Ahr .......................... 604/367 |
| 4,973,325 | A | * | 11/1990 | Sherrod et al. ............. 604/368 |
| 5,151,091 | A | * | 9/1992 | Glaug et al. .......... 604/385.101 |
| 5,304,161 | A | * | 4/1994 | Noel et al. ................... 604/378 |
| 5,662,634 | A | * | 9/1997 | Yamamoto et al. ......... 604/378 |
| 5,846,231 | A | * | 12/1998 | Fujioka et al. .............. 604/380 |
| 5,855,572 | A | * | 1/1999 | Schmidt ..................... 604/378 |
| 6,017,336 | A | * | 1/2000 | Sauer .................... 604/385.01 |
| 6,372,954 | B1 | * | 4/2002 | Johnston et al. ............ 604/378 |
| 6,569,137 | B2 | * | 5/2003 | Suzuki et al. .......... 604/385.01 |
| 2001/0014797 | A1 | | 8/2001 | Suzuki |
| 2003/0060792 | A1 | * | 3/2003 | Harriz et al. .......... 604/385.04 |
| 2004/0133178 | A1 | | 7/2004 | Otsubo |

FOREIGN PATENT DOCUMENTS

EP   1116479 A2   7/2001

(Continued)

Primary Examiner—Tatyana Zalukaeva
Assistant Examiner—Ginger Chapman
(74) Attorney, Agent, or Firm—Morrison & Foerster LLP

(57) ABSTRACT

Here is disclosed a disposable pull-on wearing article improved so that a body fluid absorbent core may be curved about a crotch region toward front and rear waist regions without forming thick creases creating a feeling of discomfort against a wearer, and wherein a concavity bulging downward may be quickly formed in the crotch region as the core is curved.

The article includes a body fluid absorbent core which includes a first core lying on a transverse middle of a crotch region and a pair of second cores lying on both sides of the first core. Front and rear end portions of the respective second cores are spaced apart from the first core by slit-like gaps and intermediate portions extending between the front and rear end portions are contiguous to the first core. Outer side edges of the respective second cores are formed with laid down V-shape cutouts.

8 Claims, 10 Drawing Sheets

| | FOREIGN PATENT DOCUMENTS | | |
|---|---|---|---|
| JP | 2548718 | 8/1996 | |
| JP | 9-173381 | 7/1997 | |
| JP | 2001-190581 A | 7/2001 | |
| JP | 2001-340383 A | 12/2001 | |
| JP | 2003-10244 A | 1/2003 | |
| WO | WO 9311727 A1 * | 6/1993 | |
| WO | WO-02/96333 A2 | 4/2002 | |

* cited by examiner

DISPOSABLE WEARING ARTICLE HAVING MULTILAYERED CORE COMPRISING CONVEX GAPS AND V-SHAPED CUTOUTS

BACKGROUND OF THE INVENTION

The present invention relates to disposable pull-on wearing articles useful in the form of disposable pull-on diapers, disposable pants for incontinent patient, disposable training pants or the like.

An invention aiming to provide a good fit wherein a crotch region of disposable wearing articles such as disposable diapers can be placed against a wearer's crotch region is disclosed in Japanese Laid-Open Patent Application No. 1997-173381 (Citation 1). In the diaper according to this disclosure, an absorbent panel comprises a first absorbent section laid at a longitudinally middle zone of the diaper and a pair of second absorbent sections laid along transversely opposite side edges of the crotch region and respectively spaced apart from the first absorbent section. Each of the second absorbent sections is formed along its side edge facing away from the first absorbent section with three-dimensional gathers. The crotch region of the diaper, when put on a wearer, presents a sectional shape as illustrated by FIG. 10 (corresponding to FIG. 4 in Citation 1). The diaper illustrated by FIG. 10 has the first absorbent section 104, the second absorbent sections 105 and the three-dimensional gathers 106. The second absorbent sections 105 rise up along the respective side edges of the first absorbent section 104 as the three-dimensional gathers 106 rise up and, in consequence, these first absorbent section 104, second absorbent sections 105, and the three-dimensional gathers 106 cooperate with one-another to form a concavity 107 bulging downward in the crotch region. This concavity 107 is available as a temporary retention space for urine discharged by the wearer until urine is completely absorbed by the absorbent panel.

An absorbent garment disclosed in Japanese Patent Publication No. 2548718 (Citation 2) also aims to provide a good fit wherein the crotch region of the garment can be placed against a wearer's crotch region. This garment has an absorbent panel and a fastening means. The absorbent panel is formed along its transversely opposite side edges with open cutouts. In a vicinity of these cutouts, the absorbent panel is provided with elastic members, and a contractile force of these elastic members deforms the absorbent panel so as to close openings of the respective cutouts. Such deformation ensures that the absorbent panel well conforms with a wearer's crotch region and a concavity bulging downward is formed in the crotch region of the garment.

The diaper disclosed in Citation 1 intends to facilitate the transversely opposite lateral zones of the absorbent panel in the crotch region, i.e., the second absorbent sections 105, to be deformed in the transverse direction by dividing the absorbent panel into the first absorbent section 104 and the second absorbent sections 105. However, upon such deformation, the absorbent panel is compressed in the longitudinal direction, describing a circular arc in the back-and-forth direction of the wearing article and forming a plurality of distinct creases. Consequently, the absorbent panel becomes bulky as the wearing article is put on the wearer in the crotch region, and such bulkiness may obstruct free movement of the wearer's legs and/or deteriorate an appearance of the article when worn by the wearer. In addition, to put the article illustrated in this Citation 1 on the wearer, the waist regions and the leg-surrounding regions should be placed closely against the wearer's corresponding regions to position the article relative to the wearer's body and then the front and rear waist regions should be connected together using fastener tapes. After the article has been put on the wearer in this manner, the crotch region may often be deformed in an inverted V-shape along the wearer's crotch region and the concavity 107 illustrated by FIG. 10 cannot be formed until after the crotch region has been gripped and pulled downward with the fingers. According to the disclosure of Citation 1, both the first absorbent section 104 and the second absorbent sections 105 are sandwiched between a liquid-pervious topsheet 101 and a liquid-impervious backsheet 102, and in boundary regions between the first and second absorbent sections 104, 105, these sheets 101, 102 are placed upon and bonded integrally. However, if any quantity of pulp particles and/or super-absorbent polymer particles is present in those boundary regions, it may be difficult or impossible to put the top- and backsheets 101, 102 in close contact with each other and to bond them together using adhesives or welding techniques, due to the presence of those particles. In the case of the absorbent panel having the top- and backsheets 101, 102 not properly bonded together in the vicinity of the first absorbent section 104 and/or second absorbent sections 105, the first absorbent section 4 and the second absorbent sections 105, particularly the second absorbent sections 105 each having a relatively small size are apt to get out of their predetermined shapes.

The garment disclosed in Citation 2 is also of the open-type and, similarly to the article disposed in Citation 1, it is difficult for the absorbent panel to be deformed so that the openings of the respective cutouts may be reliably closed, and it is also difficult for the crotch region to be formed with the concavity.

SUMMARY OF THE INVENTION

It is an object of the present invention to provide a disposable pull-on wearing article improved so that a body fluid absorbent core may be curved about a crotch region toward front and rear waist regions without forming thick creases creating a feeling of discomfort against a wearer and a concavity bulging downward may be quickly formed in the crotch region as the core is curved.

According to the present invention, there is provided a disposable pull-on wearing article having a front waist region, a rear waist region, a crotch region and a body fluid absorbent panel extending over the crotch region further into the front and rear waist regions and the body fluid absorbent panel has a longitudinal direction extending toward the front and rear waist regions and a transverse direction crossing the longitudinal direction.

The body fluid absorbent panel comprises a body fluid absorbent core having an inner surface facing a wearer's skin and an outer surface facing away from the wearer's skin and a liquid-pervious sheet covering at least the inner surface of these inner and outer surfaces and facing the wearer's skin; a portion of the core lying in at least the crotch region of those front waist region, rear waist region and crotch region comprising a first core lying on a middle as viewed in the transverse direction and a pair of second cores lying on both sides of the first core; the second cores respectively have front end portions, rear end portions and intermediate portions extending between these front and rear end portions as viewed in the longitudinal direction; the front and rear end portions are spaced apart from the first core by front and rear pairs of slit-like gaps formed between the first core and respective the second cores and extending generally in the longitudinal direction and the intermediate portions are contiguous to the first core; the second cores are formed along the transversely opposite outer side edges thereof with laid down V-shape cutouts diverging outward from the transversely opposite outer side edges; and the body fluid absorbent panel is provided in a vicinity of the outer side edges with elastic members extending in a stretched state in the longitudinal direction.

According to one preferred embodiment of the invention, the elastic members include at least one pair of thread- or ribbon-like elastomer extending across the cutouts in the longitudinal direction along the outer side edges.

According to another preferred embodiment of the invention, the core has its inner and outer surfaces wrapped with a liquid absorbent and spreading sheet and sections of the liquid absorbent and spreading sheet respectively covering the inner and outer surfaces are not bonded together in the slit-like gaps.

According to still another preferred embodiment of the invention, the article further comprises an outer cover having a resistance against permeation of body fluids and serving as a chassis for the absorbent panel so that the absorbent panel extends over the crotch region and further extends into the front and rear waist regions on the outer cover. The outer cover may be of annular configuration.

The disposable pull-on wearing article according to the present invention is primarily characterized in that the body fluid absorbent core comprises, as viewed in the transverse direction of the crotch region, the center core and the lateral cores lying on both sides of the center core and the center core and lateral cores are spaced apart one from another by the pairs of slit-like gaps formed at the zones of the core placed aside toward the front waist region and the rear waist region, respectively, but are contiguous one to another in the section defined by these pairs of slit-like gaps. This novel article is further characterized by the laid down V-shape cutouts formed on the outer side edges of the respective lateral cores so that a contractile force of the elastic members provided in the vicinity of the outer side edges of the respective lateral cores may cause the lateral cores to rise up on both sides of the center cores whereby to form the creaseless barrier walls and cooperates with the center core to form the concavity bulging downward in the crotch region. The lateral cores are partially contiguous to the center core and thereby have their positions relative to the center core reliably stabilized.

DETAILED DESCRIPTION OF THE PREFERRED EMBODIMENTS

Details of the disposable pull-on wearing article according to the present invention will be more fully understood from the description of a pull-on diaper, one of preferred embodiments, given hereunder with reference to the accompanying drawings.

Figure 1:
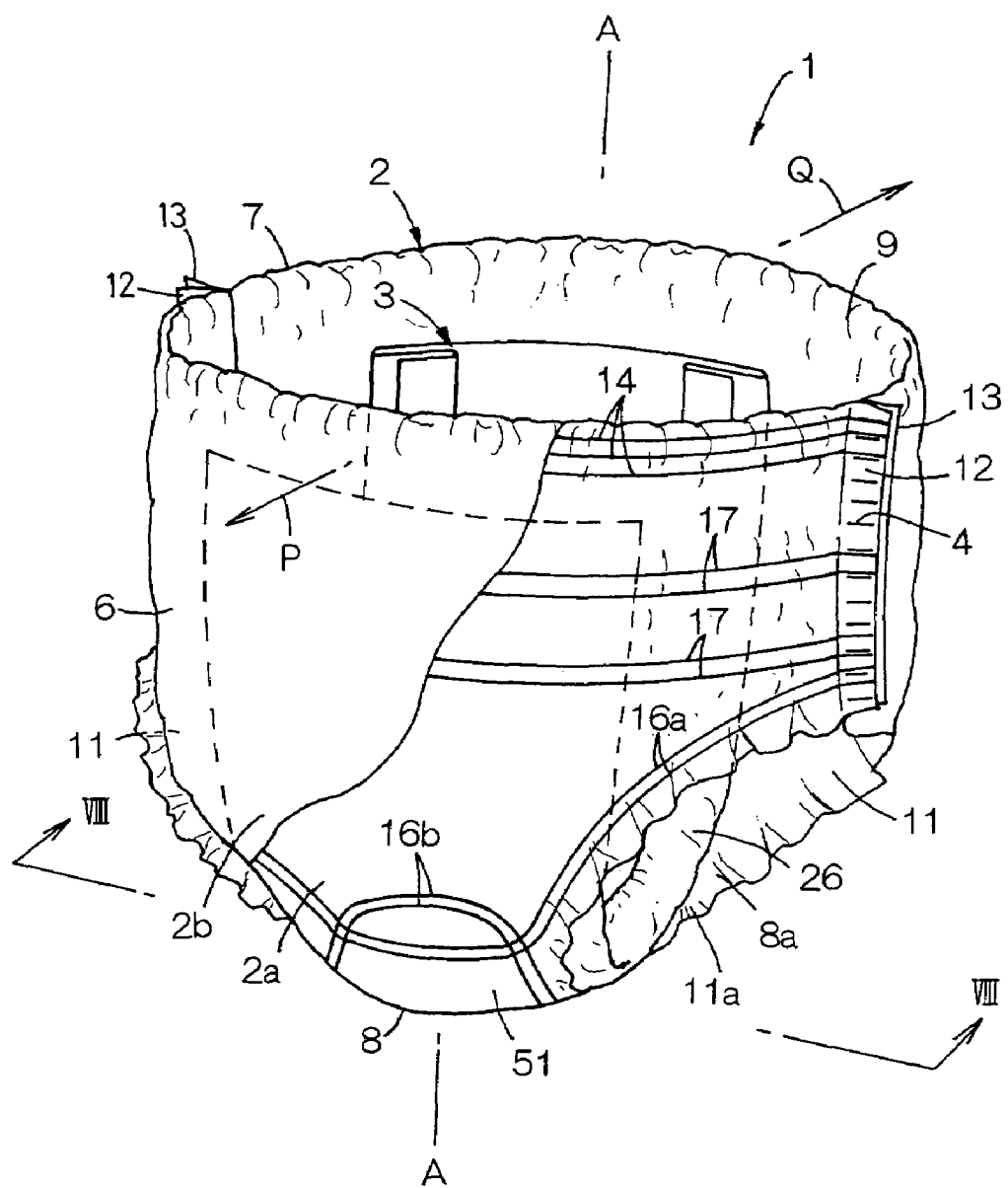
FIG. 1 is a partially cutaway perspective view depicting a disposable pull-on diaper.

In FIG. 1 is a partially cutaway perspective view depicting a disposable pull-on diaper 1. A diaper 1 is of pull-on or pants-type and preferably comprises an outer cover 2 having a resistance to permeation of body fluids and a body fluid absorbent panel 3 adapted for absorption and containment of body fluids. The term "resistance" used herein means that the outer cover 2 is absolutely or substantially impervious to body fluids during actual use of the diaper 1. The outer cover 2 comprises an inner sheet 2a and an outer sheet 2b which are identical to each other in size as well as in shape and placed upon each other and bonded together so as to define a front waist region 6, a rear waist region 7 and a crotch region 8. The front and rear waist regions 6, 7 are put flat together along respective pairs of transversely opposite side edges 12, 13 and bonded together at a plurality of spots 4 arranged intermittently in a vertical direction so as to form the diaper 1 with a waist-hole 9 and a pair of leg-holes 11. Along a peripheral edge of the waist-hole 9, a plurality of first waist elastic members 14 are interposed between the inner and outer sheets 2a, 2b and bonded in a stretched state to the inner surface of at least one of these two sheets 2a, 2b. Along peripheral edges of the respective leg-holes 11, a plurality of first leg elastic members 16a go approximately half around the one leg-hole 11 on its front side, then extend across the crotch region 8 and go approximately half around the other leg-hole 11 on its front side while a plurality of second leg elastic members 16b go approximately half around the one leg-hole 11 on its rear side, then extend across the crotch region 8 and go approximately half around the other leg-hole 11 on its rear side. These leg elastic members 16a, 16b are interposed between the inner and outer sheets 2a, 2b and bonded to the inner surface of at least one of these two sheets 2a, 2b. The first leg elastic members 16a and the second leg elastic members 16b are in a stretched state at least along partial length thereof going halfway around the respective leg-holes. Below the respective leg-holes 11, the first and second leg elastic members 16a, 16b may cross each other as illustrated or may extend across the crotch region so as to get nearer one to another but not cross each other. The front and rear waist regions 6, 7 are provided between the first waist elastic members 14, on one hand, and the first and second leg elastic members 16a, 16b, on the other hand, with a plurality of second waist elastic members 17 spaced one from another in vertical direction and extend in parallel one to another around the waist-surrounding direction. These second waist elastic members 17 are laid on the inner surface of the outer sheet 2b and, in the vicinity of the transversely opposite side edges 12, 13, interposed between the inner and outer sheets 2a, 2b and bonded in a stretched state to at least one of these sheets 2a, 2b.

Figure 2:
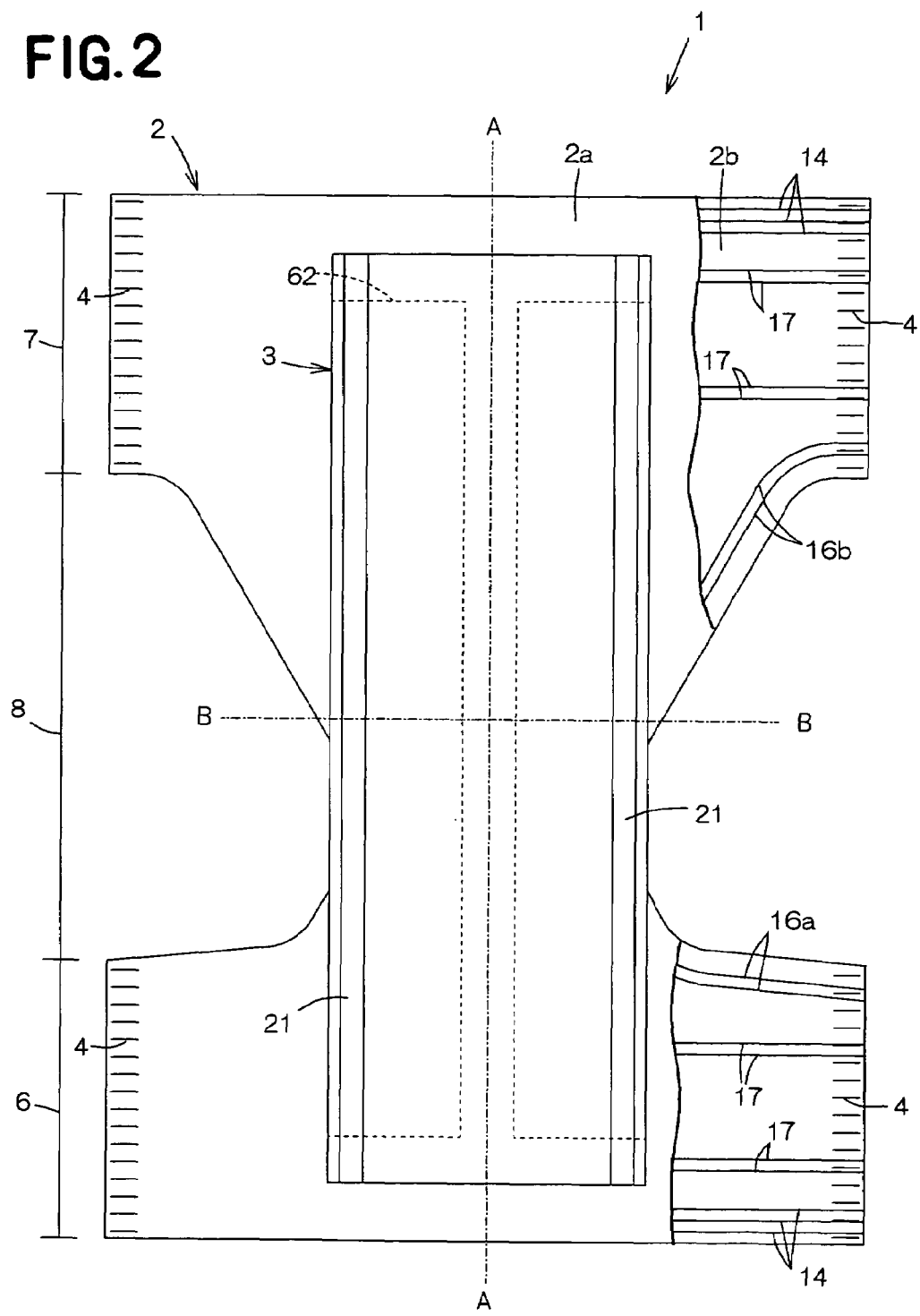
FIG. 2 is a partially cutaway plan view depicting the diaper of FIG. 1 as longitudinally developed.

FIG. 2 is a partially cut away plan view depicting the diaper 1 of FIG. 1 with the front and rear waist regions 6, 7 disconnected from each other at the spots 4 and developed forward and rearward, respectively, as indicated by arrows P, Q in FIG. 1. The outer cover 2 is generally hourglass-shaped and having the inner and outer sheets 2a, 2b bonded to each other by means of hot melt adhesives (not shown) intermittently applied on one of these two sheets 2a, 2b. The outer cover 2 has its width bisected by a longitudinal center line A-A and its length bisecting by a transverse center line B-B. As viewed in FIG. 2, the longitudinal center line A-A extends over the crotch region 8 and further into the front and rear waist regions 6, 7. The absorbent panel 3 is shaped in a rectangle extending over the crotch region 8 and further into the front and rear waist regions 6, 7 and has a longitudinal direction defined by the longitudinal center line A-A and a transverse direction defined by the transverse center line B-B. The width of the absorbent panel 3 is bisected by the longitudinal center line A-A. The absorbent panel 3 is formed along its transversely opposite side edges with barrier cuffs 21, respectively, which are elastically contractible in the longitudinal direction, i.e., parallel to the longitudinal center line A-A. The first waist elastic members 14 on the outer cover 2 extend in the waist-surrounding direction (in the transverse direction as viewed in FIG. 2) without intersecting the absorbent panel 3, while the second waist elastic members 17 extend in the waist-surrounding direction across the absorbent panel 3. The first and second leg elastic members 16a, 16b extend across the absorbent panel 3 in the crotch region 8 (See FIG. 3 also). The absorbent panel 3 is bonded at its transversely middle zone and its longitudinally opposite ends to the outer cover 2 by means of hot melt adhesives 62. The zones coated with hot melt adhesives 62 are indicated by broken lines (See FIGS. 5, 6, 7 also). Such diaper 1 shown by FIG. 2 is configured symmetrically about the longitudinal center line A-A.

Figure 3:
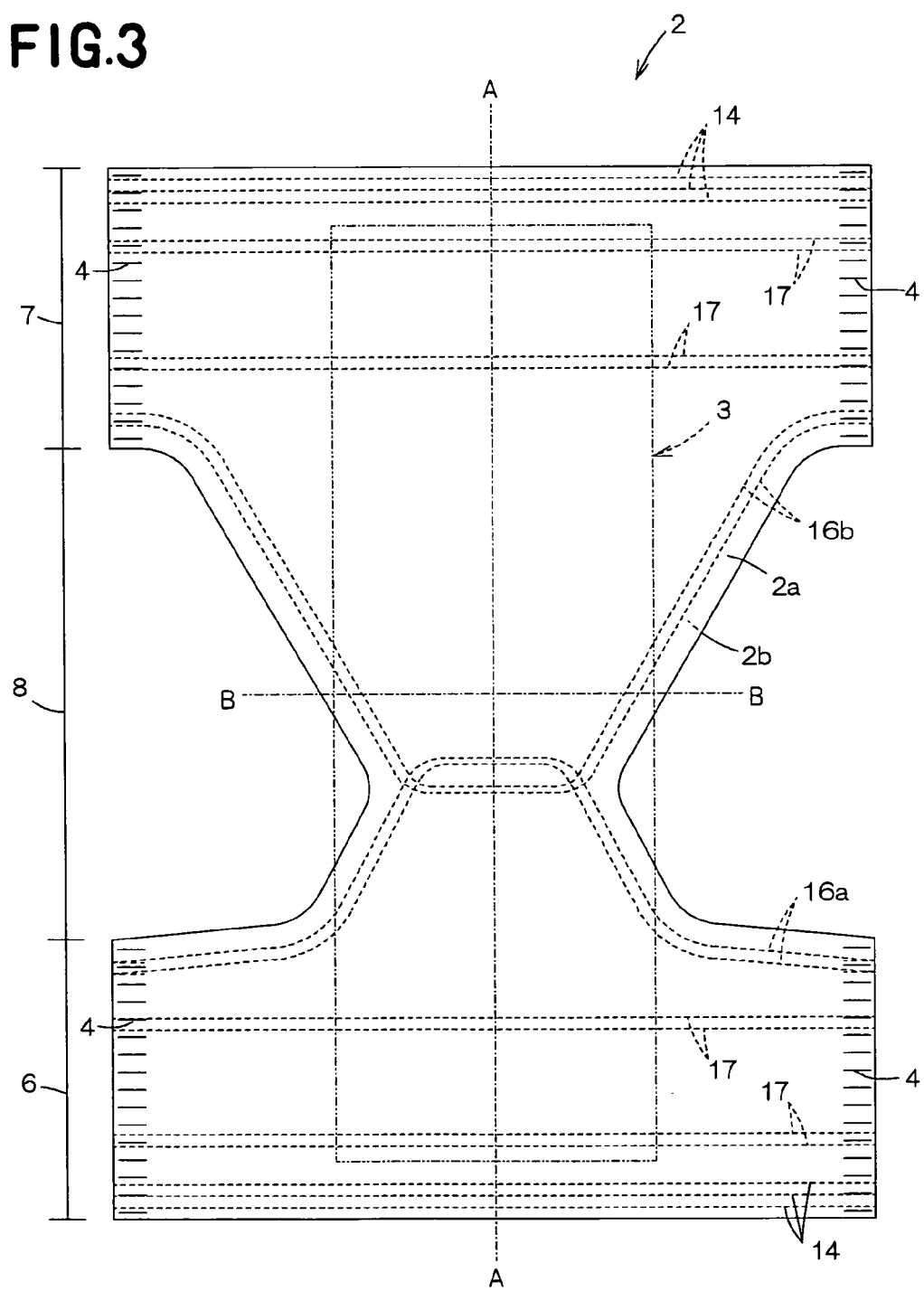
FIG. 3 is a plan view of an outer cover.

FIG. 3 is a plan view depicting the outer cover 2 of FIG. 2. In FIG. 3, the first and second waist elastic members 14, 17 as well as the first and second leg elastic members 16a, 16b interposed between the inner sheet 2a and the outer sheet 2b are indicated by chain lines and the absorbent panel 3 is indicated by chain double-dashed line.

Figure 4:
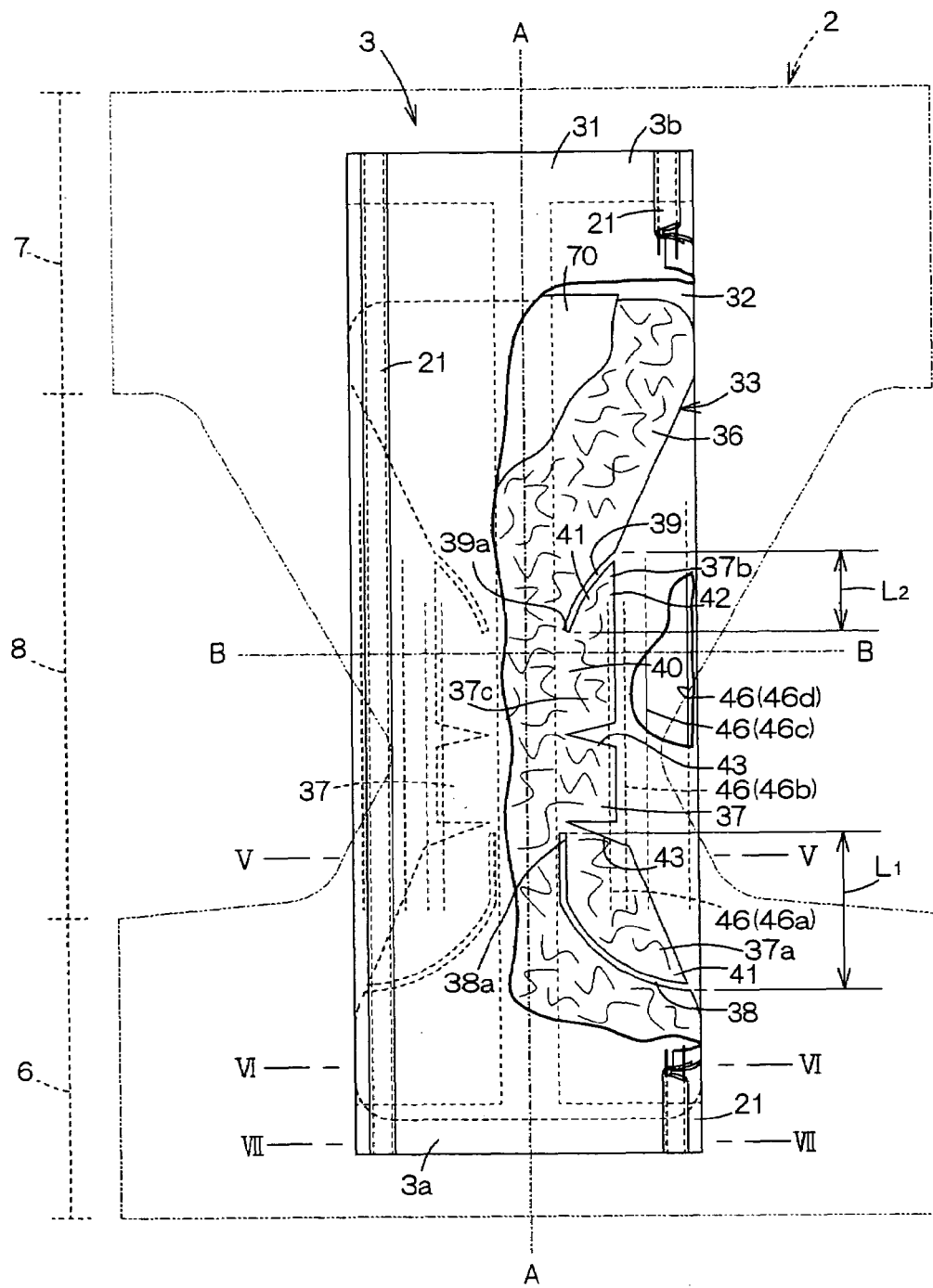
FIG. 4 is a partially cutaway plan view depicting an absorbent panel.

FIG. 4 is a partially cutaway plan view depicting the absorbent panel 3 of FIG. 2, in which the outer cover 2 is indicated by chain double-dashed line. The absorbent panel 3 comprises a liquid-pervious upper sheet 31, a liquid-impervious lower sheet 32 and a body fluid absorbent core 33 interposed between these two sheets 31, 32. The core 33 is entirely wrapped with a liquid-absorbent and spreading sheet 70 having a body fluid absorbent property and a body fluid spreading property, for example, a tissue paper (See FIGS. 5 and 6 also). The core 33 comprises a center core 36 extending on the longitudinal center line A-A from the crotch region 8 into the front and rear waist regions 6, 7 so as to gradually diverge, and left and right lateral cores 37 lying on both sides of the center core 36 in the crotch region 8, including a crossing zone of the longitudinal center line A-A and the transverse center line B-B. The center core 36 and the lateral cores 37 are partially spaced apart one from another by a pair of front slits 38 extending generally in the longitudinal direction, describing curved arcs which are convex toward the longitudinal center line A-A and a pair of rear slits 39 similar to the front slits 38. Center core 36 and lateral cores 37 are contiguous one to another at a contiguous zone 40 defined between inner ends 38a, 39a of these slits 38, 39. Each of the lateral cores 37 has inner edges 41 opposed to the center core 36 with the slits 38, 39 therebetween, an outer edge 42 extending in the longitudinal direction and defining a part of the outermost side edge of the core 33, and cutouts 43 formed in a portion of the crotch region 8 located toward the front waist region 6, each describing a V-shape tapered from the outer side edge 42 toward the longitudinal center line A-A. The inner edges 41 intersect the outer side edge 42 to define a front end 37a and a rear end 37b of the lateral core 37. An intermediate portion 37c extends between these front and rear ends 37a, 37b and defines the contiguous zone 40. In the preferred core 33, the respective slits 38, 39 have lengths $L_1$, $L_2$ extending parallel to the longitudinal center line A-A in a range of 10 to 200 mm, widths in a range of 3 to 15 mm, and a distance between the inner ends 38a, 39a, i.e., preferably in a range of 10 to 300 mm. The absorbent panel 3 including such core 33 is provided in a vicinity of the respective outer side edges 42 of the lateral cores 37 with crotch elastic members 46 extending along the outer side edges 42 in the longitudinal direction. The crotch elastic members 46 preferably comprise a plurality of, for example, first through fourth crotch elastic members 46a through 46d and at least one of these elastic members 46, for example, the first crotch elastic member 46a extends across the cutouts 43 as illustrated. Details of these crotch elastic members 46a through 46d are illustrated by FIGS. 5, 6 and 7.

Figure 5:
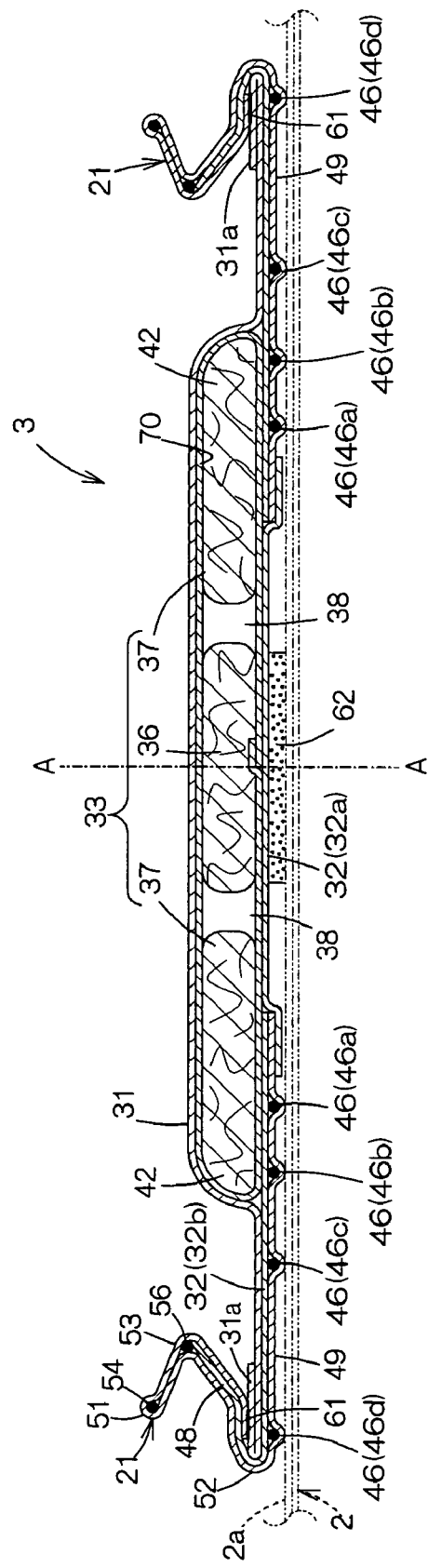
FIG. 5 is a sectional view taken along the line V-V in FIG. 4.

FIG. 5 is a sectional view taken along the line V-V in FIG. 4, in which a part of the outer cover 2 is indicated by chain double-dashed line. The upper sheet 31 covers the upper surface of the core 33 comprising the center core 36 and the pair of lateral cores 37, then extends outward beyond transversely opposite side edges of the core 33. Transversely opposite lateral portions 31a of the upper sheet 31 extending outward beyond the side edges of the core 33 are folded inward so as to be overlapped and bonded to each other by means of hot melt adhesives (not shown). The lower sheet 32 comprises a first lower sheet 32a covering the lower surface of the center core 36 as well as parts of the lower surfaces of the respective lateral cores 37 and a pair of second lower sheets 32b covering parts of the lower surfaces of the respective lateral cores 37 and extending outward beyond the respective outer side edges 42. Portions 48 of the respective second lower sheets 32b extending outward beyond the respective outer side edges 42 of the lateral cores 37 are folded inward and form parts of the respective barrier cuffs 21. Cover sheets 49 made of a nonwoven fabric are bonded to the lower surfaces of the respective second lower sheets 32b. Each of the cover sheets 49 is folded inward along a top edge 51 of the barrier cuff 21 and extends to a proximal edge 52 of the barrier cuff 21 so as to form inner and outer surfaces of the barrier cuff 21. Each of the barrier cuffs 21 contains an elastic member 54 inside its top edge 51 and an elastic member 56 inside its middle 53 defined between the top edge 51 and the proximal edge 52. These elastic members 54, 56 extend in a stretched state in the longitudinal direction as viewed in FIG. 4 and are bonded intermittently in the longitudinal direction to the inner surface of the cover sheet 49 by means of hot melt adhesives (not shown). In a vicinity of the outer side edges 42 of the lateral cores 37, the crotch elastic members 46 are interposed between the second lower sheets 32b and the cover sheet 49. The first and second crotch elastic members 46a, 46b constituting the crotch elastic members 46 underlie the respective lateral cores 37 and extend parallel to the longitudinal center line A-A (See FIG. 4). The respective third crotch elastic members 46c lie between the respective lateral cores 37 and the proximal edges 52 of the respective barrier cuffs 21 and extend parallel to the longitudinal center line A-A. Finally, the respective fourth crotch elastic members 46d lie in a vicinity of the proximal edges 52 of the respective barrier cuffs 21 and extend parallel to the longitudinal center line A-A.

In each of the barrier cuffs 21, a portion defined between the proximal edge 52 and the middle 53 is formed from the second lower sheet 32b and the cover sheet 49 covering both surfaces of the second lower sheet 32b. The second lower sheet 32b serves to make the barrier cuff 21 liquid-impervious and the cover sheet 49 serves to cover the second lower sheet 32b and thereby to provide the barrier cuffs 21 with a comfortable touch. A portion of the barrier cuff 21 defined between the middle 53 and the top edge 51 is formed from the cover sheet 49 alone, i.e., the second lower sheet 32k is not used, in order to provide this portion with a touch as flexible as possible. The elastic member 56 at the middle 53 is placed aside from the elastic member 54 at the top edge 51 toward the longitudinal center line A-A. Both the elastic member 54 and the elastic member 56 are bonded in a stretched state to the cover sheet 49 so that a contractile force of these elastic members may cause the barrier cuff 21 to rise up as illustrated. While a particular height by which the barrier cuff 21 rises up depends on particular contraction percentages of these elastic members 54, 56, the barrier cuff 21 describes a V-shape diverging outward in the transverse direction of the absorbent panel 3 as it rises up, because the elastic member 56 at the middle 53 is placed aside toward the longitudinal center line A-A. At the proximal edges 52 of the respective barrier cuffs 21, the cover sheet 49 is bonded to the respective side edges 31a of the upper sheet 31 by means of adhesives 61. The absorbent panel 3 shown in FIG. 5 is bonded to the inner sheet 2a of the outer cover 2 by means of adhesives 62 applied on the first lower sheet 32a, the second lower sheet 32b, and/or cover sheet 49. Preferably, the absorbent panel 3 is bonded to the inner sheet 2a in a region defined between each pair of the adjacent first crotch elastic members 46a in order to ensure that the absorbent panel 3 does not affect stretching and contraction of the crotch elastic members 46.

Figure 6:
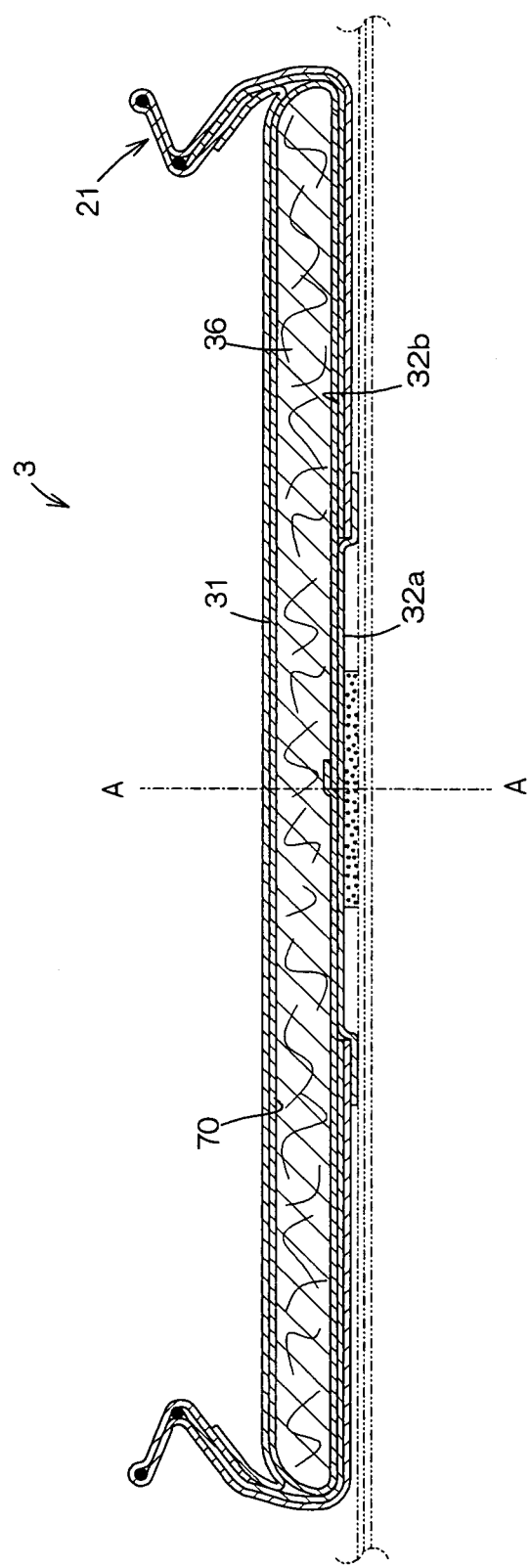
FIG. 6 is a sectional view taken along the line VI-VI in FIG. 4.
Figure 7:
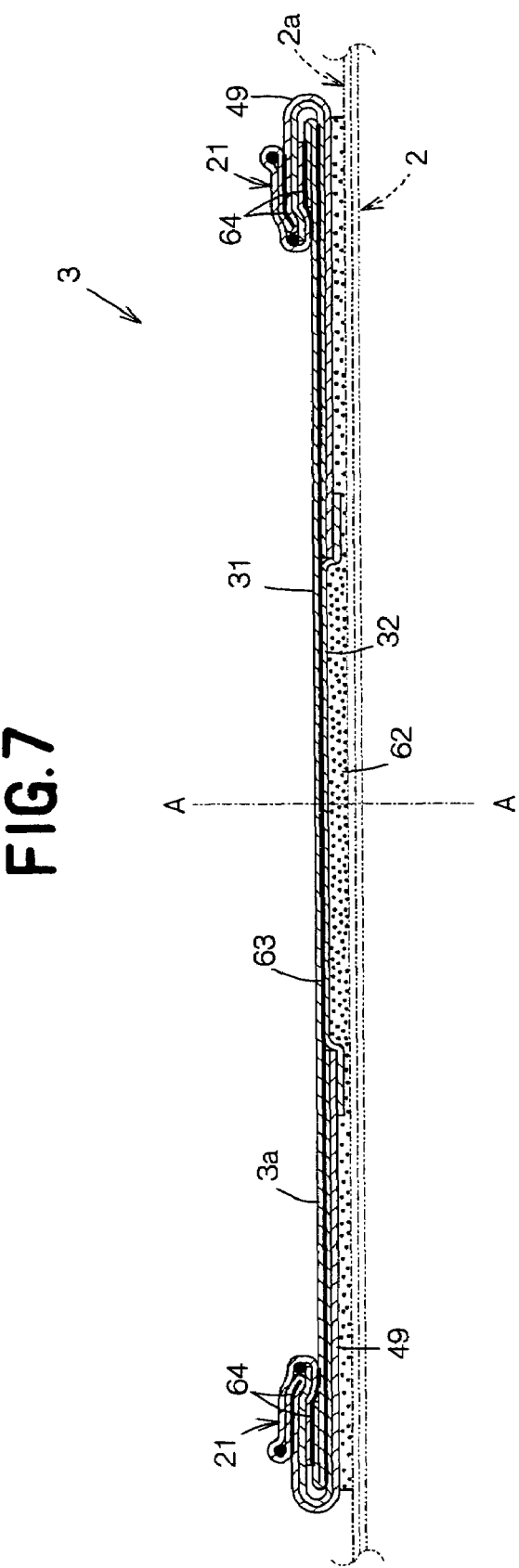
FIG. 7 is a sectional view taken along the line VII-VII in FIG. 4.

FIG. 6 is a sectional view taken along the line VI-VI in FIG. 4. As illustrated, the center core 36 extends over a full width of the absorbent panel 3 and the barrier cuffs 21 rise up on the transversely opposite side edges of this center core 36.

FIG. 7 is a sectional view taken along the line VII-VII in FIG. 4. The line VII-VII extends across a front end portion 3a of the absorbent panel 3 (See FIG. 4). The core 33 is absent in this front end portion 3a and, along this front end portion 3a, the upper sheet 31 and the lower sheet 32 are placed upon each other and bonded together by means of adhesives 63. Along this front end portion 3a, the respective barrier cuffs 21 are folded back and opposed sections of the respective barrier cuffs 21 are bonded together by means of adhesives 64 and, at the same time, the cover sheet 49 and the upper sheet 31 are bonded together by means of adhesives 64. The absorbent panel 3 is bonded to the inner sheet 2a over its full width by means of adhesives 62. A rear end portion 3b of the absorbent panel 3 presents the same cross-section as that of the front end portion 3a.

In the pull-on diaper 1 of FIG. 1 constructed as described above, the crotch elastic members 46 associated with the absorbent panel 3 and the elastic members 54, 56 associated with the barrier cuffs 21 contract as the absorbent panel 3 is curved about the crotch region 8 toward the front and rear waist regions 6, 7 generally in a U-shape. Contraction of the elastic members, particularly of the crotch elastic members 46 causes the lateral cores 37 to be deformed in a manner such that the V-shape described by each of the cutouts 43 as will be seen in FIG. 4 becomes narrower, and simultaneously the absorbent panel 3 is folded along a line extending between the inner ends 38a, 39a of the respective slits 38, 39 in the contiguous zone 40 and front and rear pairs of slits 38, 39 whereby the outer side edges 42 rise up against a wearer's inguinal region. Each of the lateral cores 37 has its front and rear ends 37a, 37b spaced apart by the slits 38, 39 from the center core 36. Such a unique arrangement allows the lateral core 37 to reduce widths of the respective cutouts 43 without being restrained by the center core 36 and thereby to reduce its longitudinal dimension along the longitudinal center line A-A. At the same time, such a unique arrangement facilitates the lateral zone 37 to rise up on the diaper 1. While the upper and lower sheets 31, 32 are formed with creases in the cutouts 43 of the lateral core 37 as these cutouts 43 become narrower, the lateral core 37 itself is free or substantially free from the formation of such creases. Consequently, there is no anxiety that the lateral cores 37 of the absorbent panel 3 each having a relatively high stiffness might be formed with creases making the panel bulky and deteriorating a good fit of the panel 3 to a wearer as well as a feeling to wear the diaper. At least one of the first crotch elastic member 46a may extend across the cutouts 43 to reliably reduce the respective cutouts 43.

Figure 8:
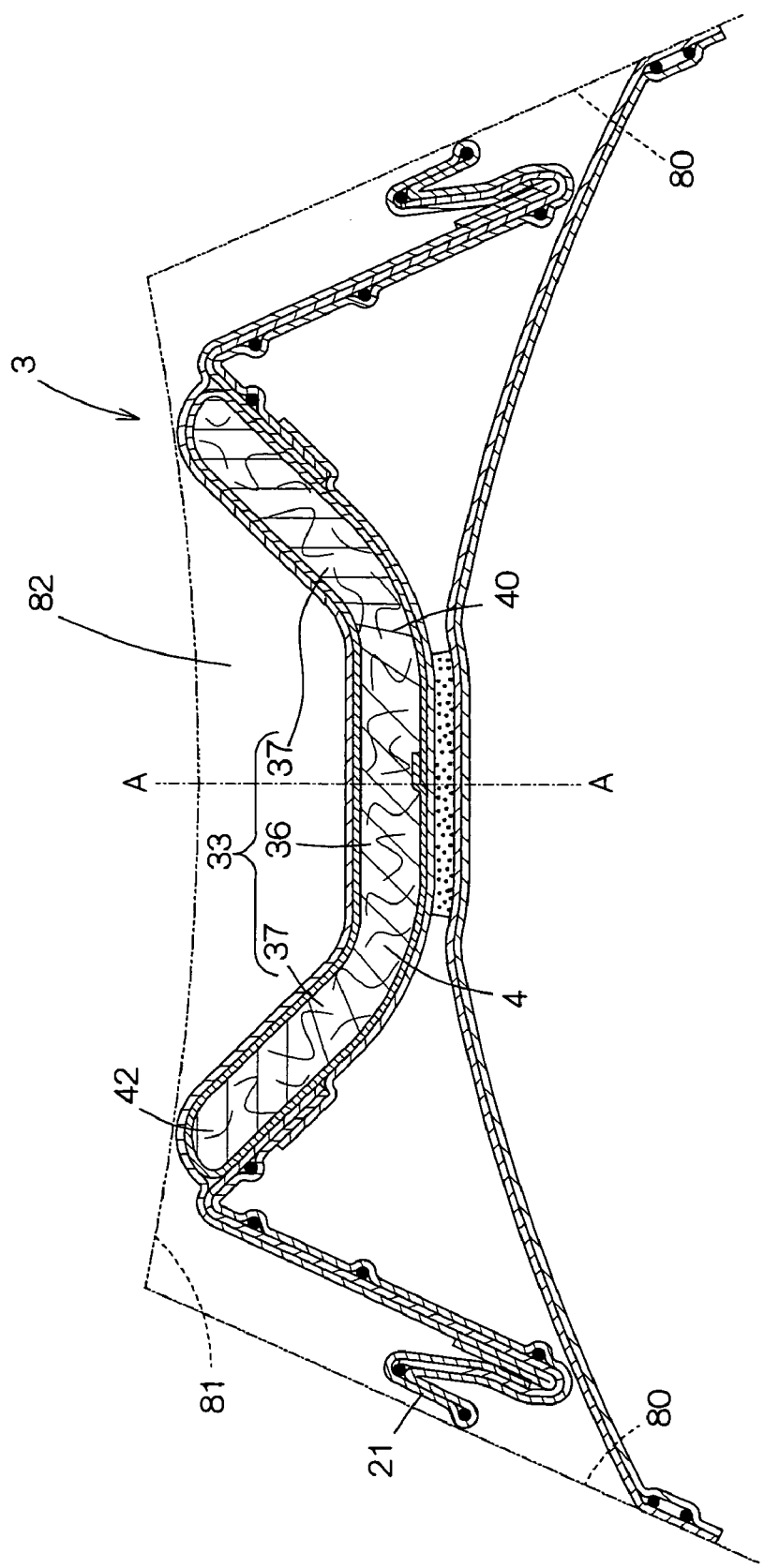
FIG. 8 is a sectional view taken along the line VIII-VIII in FIG. 1.

FIG. 8 shows an important part of a longitudinal sectional view taken along the line VIII-VIII in FIG. 1, in which the diaper wearer's legs 80 are indicated by chain double-dashed line. The line VIII-VIII is coincident with the transverse center line B-B in FIG. 2. The barrier cuffs 21 in the crotch region 8 come in contact with inner sides of the respective legs 80, the lateral cores 37 of the absorbent panel 3 rise and the center core 36 sags down as the diaper 1 is pulled upward along the legs 80 having been inserted through the respective leg-holes 11. The diaper 1 further pulled upward until the outer side edges 42 of the respective lateral cores 37 come in contact from below with the wearer's inguinal region 81. With the diaper 1 in this state, the lateral cores 37 serve as body fluid absorbent leak-barrier walls against body fluids and the center core 36 is formed in the crotch region 8 with a pocket-like concavity 82 defining a liquid-absorbent bottom. In other words, By adopting the absorbent panel 3 comprising the center core 36 and the lateral cores 37 for the pull-on diaper 1, the concavity 82 is automatically formed without the formation of deep creases in the core 33 as the diaper 1 is put on the wearer. Particularly in the case of the adult diaper 1, this concavity 82 is useful for temporary retention of a relatively large quantity of urine discharged by the wearer at once until such urine is completely absorbed by the core 33. A quantity of urine absorbed by the center core 36 which is contiguous to the lateral cores 37 in the contiguous zone 40 can spread to the lateral cores 37. Contiguousness of the center core 36 to the lateral cores 37 ensures that the positions of the respective lateral cores 37 relative to the center core 36 can be stabilized not only in the course of manufacturing the diaper 1 but also during actual use of the diaper 1. While it is also possible to make the diaper with the center core 36 and the lateral cores 37 provided separately from each other, the relatively small sized lateral cores 37 are movable relative to the center core 36 and therefore it is difficult to stabilize the entire shape of the core 33. On the contrary, in the absorbent panel 3 of the diaper 1 according to the present invention, the center core 36 is partially contiguous to the lateral cores 37, without any positive bonding between the upper sheet 31 and the lower sheet 32 in the slits 38, 39. Even when the inner and outer surfaces of the core 33 is wrapped with a liquid-absorbent and spreading sheet 70, there is no positive bonding between sections of the sheet 70 lying on the inner and outer surfaces of the core 33 along the slits 38, 39. Relative positions of these slits 38, 39 and the upper and lower sheets 31, 32 are exemplarily illustrated by FIG. 5.

Figure 9:
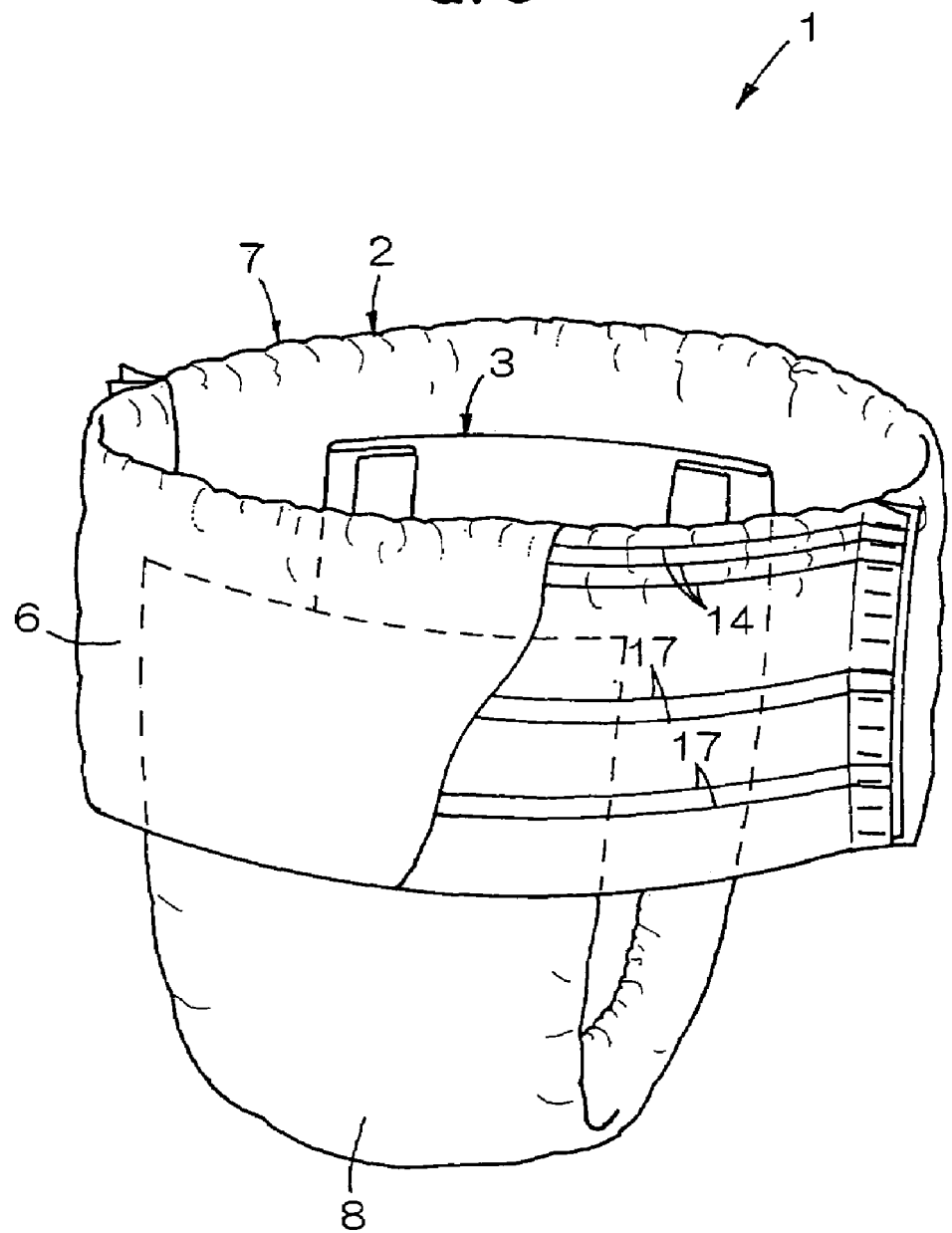
FIG. 9 is a view similar to FIG. 1 depicting an alternative embodiment of the invention.
Figure 10:
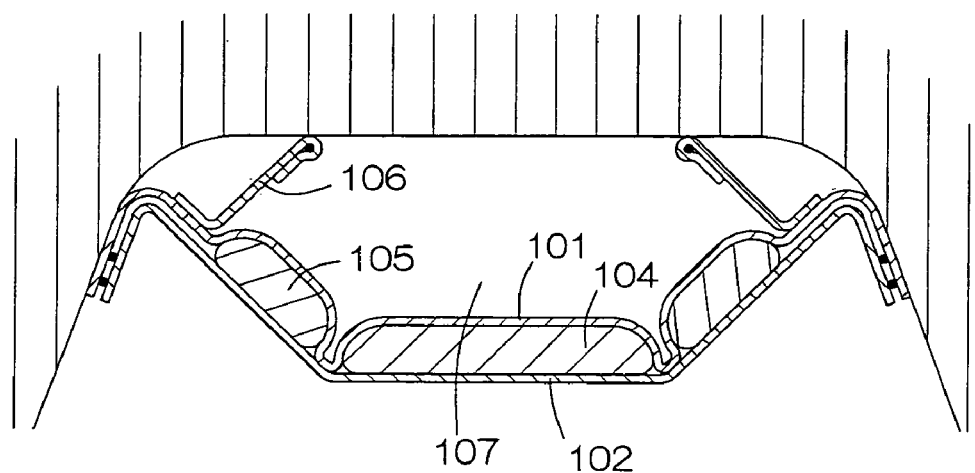
FIG. 10 is a diagram illustrating an example of prior art.

FIG. 9 is a view similar to FIG. 1 showing one preferred embodiment of the invention. The outer cover 2 of the diaper 1 shown by FIG. 9 is an annular shape defined by the front waist region 6 and the rear waist region 7 respectively provided with the first waist elastic members 14 and the second waist elastic member 17. This outer cover 2 has no crotch region. The crotch region 8 in such diaper 1 is formed by the body fluid absorbent panel 3 alone. The body fluid absorbent panel 3 lies on the inner surface of the outer cover 2 and extends over the crotch region 8 further into the front and rear waist regions 6, 7. The outer cover 2 and the body fluid absorbent panel 3 are bonded to each other in the same manner as in the case illustrated by FIGS. 6 and 7.

In the diaper 1 according to the present invention, at least one cutout 43 of the absorbent panel 3 may be formed at an appropriate position along the outer side edge 42 of the lateral core 37. Dimensions of the center core 36 in the longitudinal and transverse directions in the front and rear waist regions 6, 7 are not limited to those in the illustrated embodiment and may be appropriately varied. The upper sheet 31 may be formed from using a liquid-pervious nonwoven fabric or a liquid-pervious porous plastic film. The lower sheet 32 may be formed from using a liquid-impervious plastic film or a liquid-impervious nonwoven fabric. The cover sheet 49 covering the lower sheet 32 may be formed from using a breathable nonwoven fabric, a breathable water repellent nonwoven fabric, a liquid-impervious nonwoven fabric or the like. The core 33 may be formed using fluff pulp or a mixture of fluff pulp and super-absorbent polymer particles. Shape as well as structure of the outer cover 2 is not limited to those exemplarily illustrated and may be appropriately modified so far as it functions to hold the absorbent panel 3 in contact with the wearer's skin. For example, it is possible without departing from the scope of the invention to replace the first and second leg elastic members 16a, 16b shown in FIG. 1 by continuous elastic members which fully go round the peripheral edges of the respective leg-holes 11. Stock materials for the inner sheet 2a and the outer sheet 2b constituting the outer cover 2 may be selected from nonwoven fabrics, woven fabrics and plastic films. Stock materials for the crotch elastic members 46 and the other elastic members may be selected from thread-like or ribbon-like various kinds of elastomers. Bonding of the different members constituting the diaper 1 may be achieved using suitable adhesives or suitable welding techniques.

While the present invention has been described above on the basis of an embodiment of the disposable pull-on diaper 1, the present invention is applicable also to pants for incontinent patient, training pants or the like.

What is claimed is:

1. A disposable pull-on wearing article having a longitudinal axis and a transverse axis, said article comprising:
   a front waist region;
   a rear waist region;
   a crotch region;
   an outer cover;
   a body fluid absorbent panel being bonded at a transversely middle zone thereof and at longitudinally opposite ends to said outer cover and extending over said crotch region further into said front and rear waist regions, said body fluid absorbent panel having a longitudinal direction extending toward said front and rear waist regions and a transverse direction crossing said longitudinal direction,
   said body fluid absorbent panel comprising a body fluid absorbent core having an inner surface facing a wearer's skin and an outer surface facing away from said wearer's skin and a liquid-pervious sheet covering at least said inner surface of said inner surface and facing said wearer's skin;
   said core traversing said crotch region and extending into said front waist region and into said rear waist region, and comprising a central portion extending longitudinally from said front waist region through said crotch region into said rear waist region, said core also comprising two lateral portions, each lying on opposite lateral sides of said central portion;
   said lateral portions each having a front end region, a rear end region and an intermediate region between front and rear end regions as viewed in said longitudinal direction;
   said front and rear end regions being spaced apart from said central portion by front and rear pairs of slit-like gaps formed in said core between said central portion and said lateral portions and extending in an arc from lateral edges of said core toward said longitudinal axis and toward said transverse axis, and said intermediate region of each lateral portion being contiguous to and continuous with said central portion;
   wherein an outer side edge of said intermediate region of each lateral portion defines a plurality of V shaped cutouts whose vertices point toward said longitudinal axis, and whose sides diverge from one another as they extend away from said longitudinal axis; and
   said body fluid absorbent panel being provided in a vicinity of said outer side edges with elastic members extending in a stretched state in said longitudinal direction.

2. The disposable pull-on wearing article according to claim 1, wherein said elastic members include at least one pair of thread- or ribbon-like elastomer extending across said cutouts in said longitudinal direction along said outer side edges.

3. The disposable pull-on wearing article according to claim 1, wherein said core has inner and outer surfaces thereof wrapped with a liquid absorbent and spreading sheet and sections of said liquid absorbent and spreading sheet respectively covering said inner and outer surfaces are not bonded together in said slit-like gaps.

4. The disposable pull-on wearing article according to claim 1, further comprising an outer cover having a resistance against permeation of body fluids and serving as a chassis for said absorbent panel so that said absorbent panel extends over said crotch region and further extends into said front and rear waist regions on said outer cover.

5. The disposable pull-on wearing article according to claim 4, wherein said outer cover is of annular configuration.

6. A disposable pull-on wearing article having a longitudinal axis and a transverse axis, said article comprising:
   a front waist region;
   a rear waist region;
   a crotch region;
   an outer cover;
   a body fluid absorbent panel being bonded at a transversely middle zone thereof and at longitudinally opposite ends thereof to said outer cover and extending over said crotch region further into said front and rear waist regions;
   said body fluid absorbent panel comprising a body fluid absorbent core having an inner surface facing a wearer's skin and an outer surface facing away from said wearer's skin and a liquid-pervious sheet covering at least said inner surface of said inner and outer surfaces and facing said wearer's skin;

said core traversing said crotch region and extending into said front waist region and comprising a center segment and two lateral segments, each lying on opposite lateral sides of said central segment and which are shorter in dimensions than said central segment in a longitudinal direction along said longitudinal axis;

said lateral segments respectively having front end portions, rear end portions and intermediate portions extending between these front and rear end portions as viewed in said longitudinal direction;

said front and rear end portions of said lateral segments being spaced apart from said central segment by front and rear pairs of slit-like gaps formed in said core between said central segment and respective said lateral segments and extending in an arc from lateral edges of said core toward said longitudinal axis in the longitudinal direction of said longitudinal axis, and said intermediate portions of said lateral segments being contiguous to said central segment;

said intermediate portion being formed along said transversely opposite outer side edges thereof between terminal ends of said slit-like gaps with laid down V-shape cutouts whose vertices point toward said longitudinal axis, and whose sides diverge from one another as they extend away from said longitudinal axis; and said body fluid absorbent panel being provided in a vicinity of said outer side edges with elastic members extending in a stretched state in said longitudinal direction.

7. The disposable pull-on wearing article according to claim 6, wherein opposite lateral sides of said center segment gradually diverge from one another with distance from said longitudinal axis.

8. A disposable pull-on wearing article having a longitudinal axis and a transverse axis, said article comprising:

a front waist region;
a rear waist region;
a crotch region;
a body fluid absorbent panel extending over said crotch region into said front and rear waist regions;
said body fluid absorbent panel comprising a body fluid absorbent core;
said core extends over said crotch region and into said front and rear waist regions, said core comprising a central portion, extending longitudinally from said front waist region through said crotch region into said rear waist region, said central portion having a transverse width that gradually increases with distance away from a center of said crotch region so that said transverse width of said central portion is greater in said front waist region and said rear waist region than in said crotch region;
said core also comprising two lateral portions, each lying on opposite lateral sides of said central portion; said lateral portions being shorter in a longitudinal direction than said central portion, and being continuous with said central portion in at least a region of said transverse axis;
said intermediate region of each said lateral portions being continuous with said central portion,
wherein lateral edges of said core define forward and rearward pairs of channels extending in arcs toward said longitudinal and transverse axes and which together define a partial border between said center segment and said lateral segments, and
wherein outside lateral edges of said lateral portions define a plurality of V-shaped cutouts whose vertices point toward said longitudinal axis, and whose sides diverge from one another as they extend away from said longitudinal axis.

* * * * *